United States Patent
Lee (10) Patent No.: US 12,105,073 B2
(45) Date of Patent: Oct. 1, 2024

(54) METHOD OF GENERATING ABNORMAL STATE DETECTION MODEL

(71) Applicant: MOVIC LAB INC., Incheon (KR)

(72) Inventor: Won Keun Lee, Incheon (KR)

(73) Assignee: MOVIC LAB INC., Incheon (KR)

( * ) Notice: Subject to any disclaimer, the term of this patent is extended or adjusted under 35 U.S.C. 154(b) by 402 days.

(21) Appl. No.: 17/543,141

(22) Filed: Dec. 6, 2021

(65) Prior Publication Data

US 2022/0128534 A1 Apr. 28, 2022

Related U.S. Application Data

(63) Continuation of application No. PCT/KR2021/005656, filed on May 6, 2021.

(30) Foreign Application Priority Data

Oct. 28, 2020 (KR) .................. 10-2020-0141605

(51) Int. Cl.
G01N 33/00 (2006.01)

(52) U.S. Cl.
CPC ....... *G01N 33/0034* (2013.01); *G01N 33/004* (2013.01)

(58) Field of Classification Search
None
See application file for complete search history.

(56) References Cited

U.S. PATENT DOCUMENTS

| | | |
|---|---|---|
| 2010/0098429 A1 | 4/2010 | Jun et al. |
| 2012/0072173 A1 | 3/2012 | Yuan |
| 2020/0054905 A1 | 2/2020 | Livchak et al. |

FOREIGN PATENT DOCUMENTS

| | | | | |
|---|---|---|---|---|
| EP | 3358508 A1 | * | 8/2018 | .......... G06F 11/3447 |
| JP | 2019-074837 A | | 5/2019 | |
| JP | 2020-521193 A | | 7/2020 | |
| KR | 10-0726206 B1 | | 6/2007 | |
| KR | 10-2008-0051452 A | | 6/2008 | |
| KR | 10-2020-0087299 A | | 7/2020 | |

OTHER PUBLICATIONS

International Search Report issued in PCT/KR2021/005656; mailed Feb. 4, 2022.

* cited by examiner

*Primary Examiner* — Daniel S Larkin (74) *Attorney, Agent, or Firm* — Studebaker & Brackett PC (57) ABSTRACT

A method for generating an abnormal state detection model, that includes: receiving first and second normal state signals detected, for a predetermined time by first and second sensors, respectively; generating a normal state data set based on the first and the second normal state signals; recognizing first and second variable values; generating a first abnormal state signal by applying the first variable value to an impulse function and a second abnormal state signal by applying the second variable value to a Gaussian distribution function; generating an abnormal state data set based on the first and second abnormal state signals; generating a detection model learning set for generating an abnormal state detection model by combining the normal state data set and the abnormal state data set; and generating an abnormal state detection model based on the detection model learning set.

15 Claims, 6 Drawing Sheets

METHOD OF GENERATING ABNORMAL STATE DETECTION MODEL

CROSS-REFERENCE TO RELATED APPLICATIONS

The present application is a continuation of International Patent Application No. PCT/KR2021/005656, filed on May 6, 2021, which is based upon and claims the benefit of priority to Korean Patent Application No. 10-2020-0141605, filed on Oct. 28, 2020. The disclosures of the above-listed applications are hereby incorporated by reference herein in their entirety.

BACKGROUND

Field

The present disclosure relates to a method of generating an abnormal state detection model, and more particularly, to a method of generating an abnormal state detection model for generating an abnormal state model that may be detected by various types of sensors.

Description of Related Art

In general, various sensors are used to measure various environmental changes, such as detecting a failure that may occur in an industrial site or monitoring a fire. There are so many different types of sensors and many commercial products are on the market, and each sensor may be incorporated to detect a failure or fire with a comprehensive view. Meanwhile, in order for these various sensors to provide accurate sensing information to users, it is necessary to learn and distinguish between a normal state and an abnormal state.

In order to learn normal and abnormal states, models for normal and abnormal states are required, respectively, and these normal and abnormal states vary depending on an environment in which a sensor is installed.

Therefore, there is a need for a method capable of generating a model for learning normal and abnormal states for various sensors in a general industrial field.

SUMMARY

An aspect of the present disclosure may provide a method of generating an abnormal state detection model, capable of providing a model for an abnormal state that may be detected by various types of sensors.

In an aspect, a method of generating an abnormal state detection model by a computer system including a processor for receiving signals from a first sensor and a second sensor, includes: a normal state receiving operation in which the processor receives a first normal state signal detected by the first sensor for a predetermined time and a second normal state signal detected by the second sensor for the predetermined time; a normal state data set generating operation in which the processor generates a normal state data set based on the first normal state signal and the second normal state signal; an abnormal state variable value recognizing operation in which the processor recognizes a first variable value and a second variable value; an abnormal state signal generating operation in which the processor generates a first abnormal state signal corresponding to the first normal state signal by applying the first variable value to an impulse function and generates a second abnormal state signal corresponding to the second normal state signal by applying the second variable value to a Gaussian distribution function; an abnormal state data set generating operation in which the processor generates an abnormal state data set based on the first abnormal state signal and the second abnormal state signal; a learning set generating operation in which the processor generates a detection model learning set for generating an abnormal state detection model by combining the normal state data set and the abnormal state data set; and an abnormal state detection model generating operation in which the processor generates an abnormal state detection model based on the detection model learning set.

In the method of generating an abnormal state detection model according to an embodiment of the present disclosure, the first sensor may be an infrared sensor and the second sensor may be a carbon dioxide detection sensor.

In the method of generating an abnormal state detection model according to an embodiment of the present disclosure, the first abnormal state signal may be a signal that models a signal detecting an occurrence of at least one of flame, spark, and arc by the first sensor.

In the method of generating an abnormal state detection model according to an embodiment of the present disclosure, the second abnormal state signal may be a signal that models a signal detecting an occurrence of at least one of smoke and combustion gas by the second sensor.

In the method of generating an abnormal state detection model according to an embodiment of the present disclosure, the computer system may be a fire detection system.

In the method of generating an abnormal state detection model according to an embodiment of the present disclosure, the first variable value may be a coefficient value of the impulse function, and in the abnormal state signal generating operation, the processor may generate the first abnormal state signal by multiplying the first variable value by the impulse function.

In the method of generating an abnormal state detection model according to an embodiment of the present disclosure, the second variable value may be at least one of a mean and a variance of the Gaussian distribution function, and in the abnormal state signal generating operation, the processor may specify a form of the Gaussian distribution function by applying the second variable value.

In the method of generating an abnormal state detection model according to an embodiment of the present disclosure, the first variable value and the second variable value may each include information on an occurrence time and frequency of the first abnormal state signal and the second abnormal state signal.

The method of generating an abnormal state detection model according to an embodiment of the present disclosure may further include: a test set generating operation in which the processor generates a detection model test set by combining the normal state data set and the abnormal state data set; and an abnormal state detection model test operation in which the processor tests the abnormal state detection model using the detection model test set.

In the method of generating an abnormal state detection model according to an embodiment of the present disclosure, the detection model learning set and the detection model test set may have different combination ratios of the normal state data set and the abnormal state data set.

In the method of generating an abnormal state detection model according to an embodiment of the present disclosure, the abnormal state variable value recognizing operation may include an operation in which the processor receives the first variable value and the second variable value input to an input unit.

In the method of generating an abnormal state detection model according to an embodiment of the present disclosure, the abnormal state variable value recognizing operation may include an operation in which the processor generates the first variable value and the second variable value from the normal state data set.

In the method of generating an abnormal state detection model according to an embodiment of the present disclosure, in the variable value recognizing operation, the processor may further recognize a third variable value, and in the abnormal state signal generating operation, the processor may apply the third variable value instead of at least one of the first variable value and the second variable value in at least one of the first abnormal state signal and the second abnormal state signal, and apply a step function instead of at least one of the impulse function and the Gaussian distribution function.

In the method of generating an abnormal state detection model according to an embodiment of the present disclosure, whether the processor applies the third variable value and the step function may be determined based on at least one of the first normal state signal and the second normal state signal in the abnormal state signal generating operation.

In an aspect, a computer system for generating an abnormal state detection model includes an input unit; a communication unit; and a processor configured to receive a signal from a first sensor and a second sensor, wherein the processor is configured to receive a first normal state signal detected by the first sensor for a predetermined time and a second normal state signal detected by the second sensor for a predetermined time, generate a normal state data set based on the first normal state signal and the second normal state signal, receive a first variable value and a second variable value received by the input unit, generate a first abnormal state signal corresponding to the first normal state signal by applying the first variable value to an impulse function, generate a second abnormal state signal corresponding to the second normal state signal by applying the second variable value to a Gaussian distribution function, generate an abnormal state data set based on the first abnormal state signal and the second abnormal state signal, generate a detection model learning set for generating an abnormal state detection model by combining the normal state data set and the abnormal state data set, and generate an abnormal state detection model based on the detection model learning set.

The method of generating an abnormal state detection model according to an embodiment of the present disclosure has an effect of enabling various sensors to learn an abnormal state by generating a model for the abnormal state that may be detected by the various sensors.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION

Hereinafter, embodiments of the present disclosure are described in detail with reference to the accompanying drawings. In describing the present disclosure, if it is determined that a detailed description of known functions and components associated with the present disclosure unnecessarily obscure the gist of the present disclosure, the detailed description thereof is omitted. The terms used henceforth are used to appropriately express the embodiments of the present disclosure and may be altered according to a person of a related field or conventional practice. Therefore, the terms should be defined on the basis of the entire content of this disclosure.

Technical terms used in the present specification are used only in order to describe specific exemplary embodiments rather than limiting the present disclosure. The terms of a singular form may include plural forms unless referred to the contrary. It will be further understood that the terms "comprise" and/or "comprising," when used herein, specify the presence of stated features, integers, steps, operations, elements, and/or components, but do not preclude the presence or addition of one or more other features, regions, integers, steps, operations, elements, components, and/or groups thereof.

In the present disclosure, a communication method of a network 40 is not limited, and each component may not be connected in the same network method. The network 40 may include not only a communication method using a communication network (e.g., a mobile communication network, a wired Internet, a wireless Internet, a broadcasting network, a satellite network, etc.) but also short-range wireless communication between devices. For example, the network 40 may include all communication methods through which objects may network, and is not limited to wired communication, wireless communication, 3G, 4G, 5G, or other methods. For example, a wired and/or network may refer to a communication network based on one or more communication methods selected from the group consisting of a local area network (LAN), a metropolitan area network (MAN), a global system for mobile network (GSM), an enhanced data GSM environment (EDGE), high speed downlink packet access (HSDPA), wideband code division multiple access (W-CDMA), code division multiple access (CDMA), time division multiple access (TDMA), Bluetooth, Zigbee, Wi-Fi, voice over Internet protocol (VoIP), LTE Advanced, IEEE802.16m, wirelessMAN-Advanced, HSPA+, 3GPP long term evolution (LTE), mobile WiMAX (IEEE 802.16e), UMB (formerly EV-DO Rev. C), flash-OFDM, iBurst and MBWA (IEEE 802.20) systems, HIPERMAN, beam-division multiple access (BDMA), world interoperability for microwave access (Wi-MAX), and ultrasonic-based communication, but is not limited thereto.

In the present disclosure, the normal state refers to a state in which an element to be detected by a sensor is within a normal range. In addition, an abnormal state refers to a case in which an element to be detected by the sensor is out of a normal range.

Hereinafter, a method of generating an abnormal state detection model according to an embodiment of the present disclosure is described with reference to FIGS. 1 to 6.

The present disclosure relates to a method and system for generating an abnormal state detection model for an abnormal state that may be detected by various types of sensors.

The method of generating an abnormal state detection model of the present disclosure is performed by a computer system 1.

Figure 1:
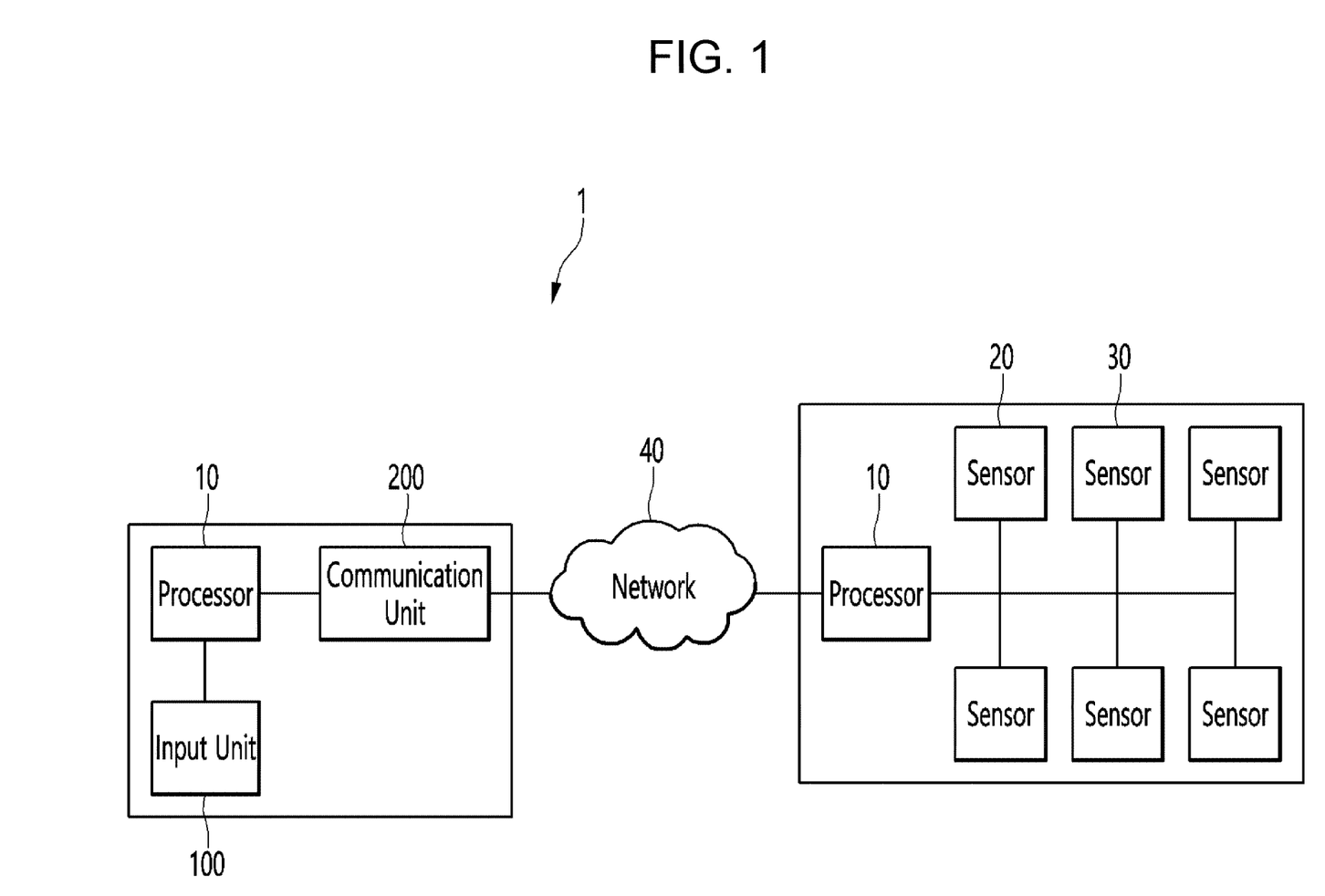
FIG. 1 is a block diagram of a computer system according to an embodiment of the present disclosure.

FIG. 1 is a block diagram of a computer system 1 according to an embodiment of the present disclosure.

Referring to FIG. 1, a computer system 1 includes a processor 10, a communication unit 200, and an input unit 100. The computer system 1 may communicate with a first sensor 20 and a second sensor 30 via a network 40.

Hereinafter, the function of each component is described.

The processor 10 generates normal state and abnormal state data sets based on an input value of a sensor input through the communication unit 200. The processor 10 generates a detection model learning set for generating an abnormal state detection model by combining the generated normal state and anomaly data sets. The processor 10 may be directly connected to the first sensor 20 and the second sensor 30 or may be connected to the first sensor 20 and the second sensor 30 through the network 40 and the communication unit 200. The communication unit 200 is connected to the network 40 to receive an input value from the sensor and transfer the received input value to the processor 10. The input unit 100 receives an input value input by a user and transfers the received input value to the processor 10.

A more specific function of each component is described in detail below while explaining a method of generating an abnormal state detection model.

Hereinafter, each step of the method of generating an abnormal state detection model according to an embodiment of the present disclosure is described.

The sensor described in the present disclosure may sense temperature, humidity, infrared rays, carbon dioxide, etc., but is not limited thereto and may be any sensor capable of detecting an external environment. Hereinafter, it is assumed that the sensor of the present disclosure is a sensor for detecting infrared rays and carbon dioxide for the convenience of description.

Figure 2:
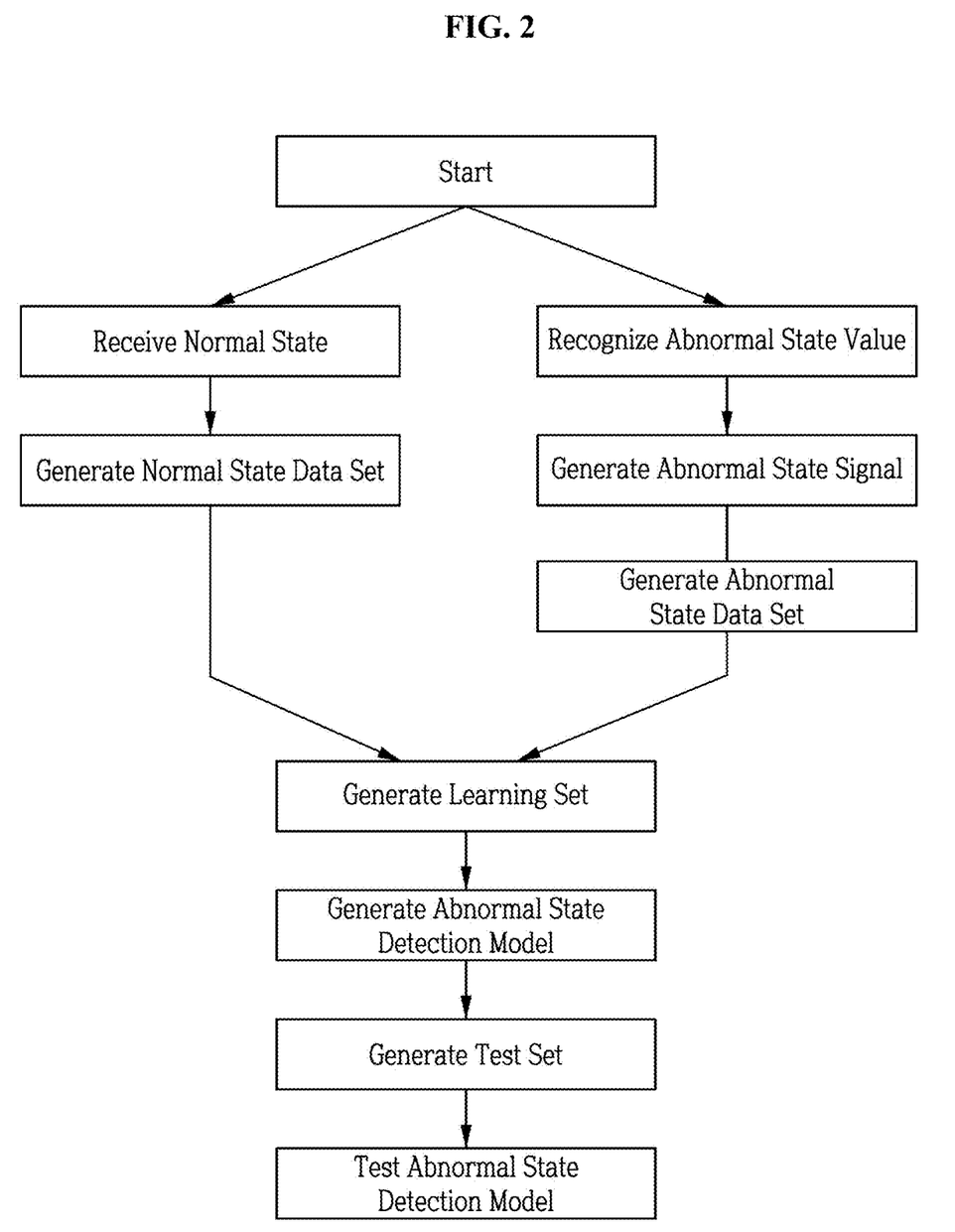
FIG. 2 is a flowchart of a method of generating an abnormal state detection model according to an embodiment of the present disclosure.

FIG. 2 is a flowchart of a method of generating an abnormal state detection model according to an embodiment of the present disclosure.

Referring to FIG. 2, the method of generating an abnormal state detection model according to an embodiment of the present disclosure includes a normal state receiving operation in which the processor 10 receives a first normal state signal detected by the first sensor 20 for a predetermined time and a second normal state signal detected by the second sensor 30 for the predetermined time, a normal state data set generating operation in which the processor 10 generates a normal state data set based on the first normal state signal and the second normal state signal, an abnormal state variable value recognizing operation in which the processor 10 recognizes a first variable value and a second variable value, an abnormal state signal generating operation in which the processor 10 generates a first abnormal state signal corresponding to the first normal state signal by applying the first variable value to an impulse function and generates a second abnormal state signal corresponding to the second normal state signal by applying the second variable value to a Gaussian distribution function, an abnormal state data set generating operation in which the processor 10 generates an abnormal state data set based on the first abnormal state signal and the second abnormal state signal, a learning set generating operation in which the processor 10 generates a detection model learning set for generating an abnormal state detection model by combining the normal state data set and the abnormal state data set, and an abnormal state detection model generating operation in which the processor 10 generates an abnormal state detection model based on the detection model learning set.

Each of the operations may be performed irrespective of the listed order, except for a case in which the operations should be performed in the listed order due to a special causal relationship. However, hereinafter, for convenience of description, it is assumed that each of the operations described above is performed in the listed order.

First, referring to FIG. 2, the normal state receiving operation in which the processor 10 receives the first normal state signal detected by the first sensor 20 for a predetermined time and a second normal state signal detected by the second sensor 30 for a predetermined time is described. As described above, the first sensor 20 or the second sensor 30 transfer a value obtained by measuring a detection element such as infrared rays or carbon dioxide to the processor 10. Here, an input value may vary depending on the type of sensor, and may be based on an analog method or a digital method. For example, in the case of the analog method, an input value of a specific sensor may be input within a range of 0 V to 5.0 V. The input value may be a value measured by the sensor itself or a value obtained by converting the value measured by the sensor by a predetermined ratio.

Figure 3:
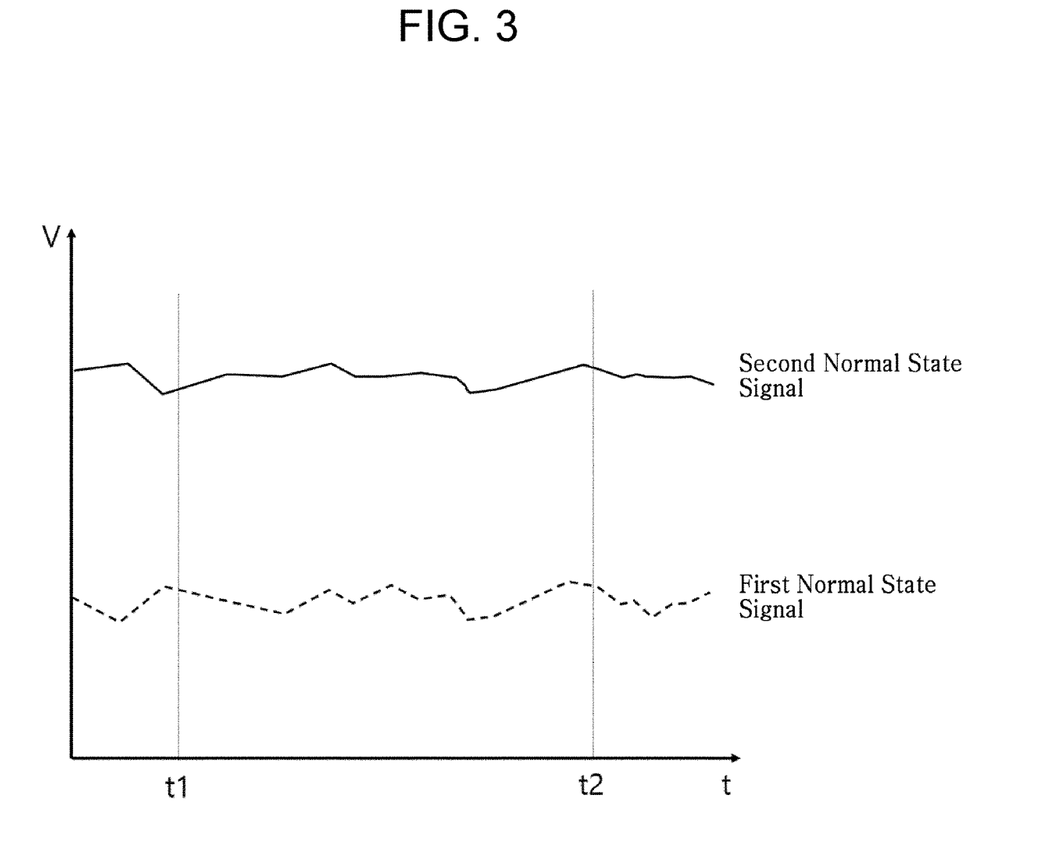
FIG. 3 is a view illustrating a first normal state signal and a second normal state signal according to an embodiment of the present disclosure.

FIG. 3 illustrates that the processor 10 receives a first normal state signal detected by the first sensor 20 for a predetermined time and a second normal state signal detected by the second sensor 30 for the predetermined time. Here, the predetermined time refers to a time from an initial time point t1 to an end time point t2 as shown in FIG. 3. The first sensor 20 or the second sensor 30 detects infrared rays or carbon dioxide from before the time point t1, and continues to detect even after the time point t2, and the processor 10 receives the first normal state signal and the second normal state signal input from the time point t1 to the time point t2. As shown in FIG. 3, the first normal state signal and the second normal state signal are changed only within a certain range in which the measurement values are constant.

Next, a normal state data set generating operation in which the processor 10 generates a normal state data set based on the first normal state signal and the second normal state signal is described with reference to FIG. 3. As described above, the processor 10 receives the first normal state signal and the second normal state signal for the predetermined time, and generates a normal state data set obtained by converting the received signal into constant data. The generated normal state data set reflects the measured values of the environment in which the sensor is installed as a detection target, so the normal state data set is considered to reflect a normal state of the environment in which the sensor is installed, as it is. In addition, the normal state data set may be used as a basis for determining a signal deviating from the normal state data set as being in an abnormal state.

Figure 4:
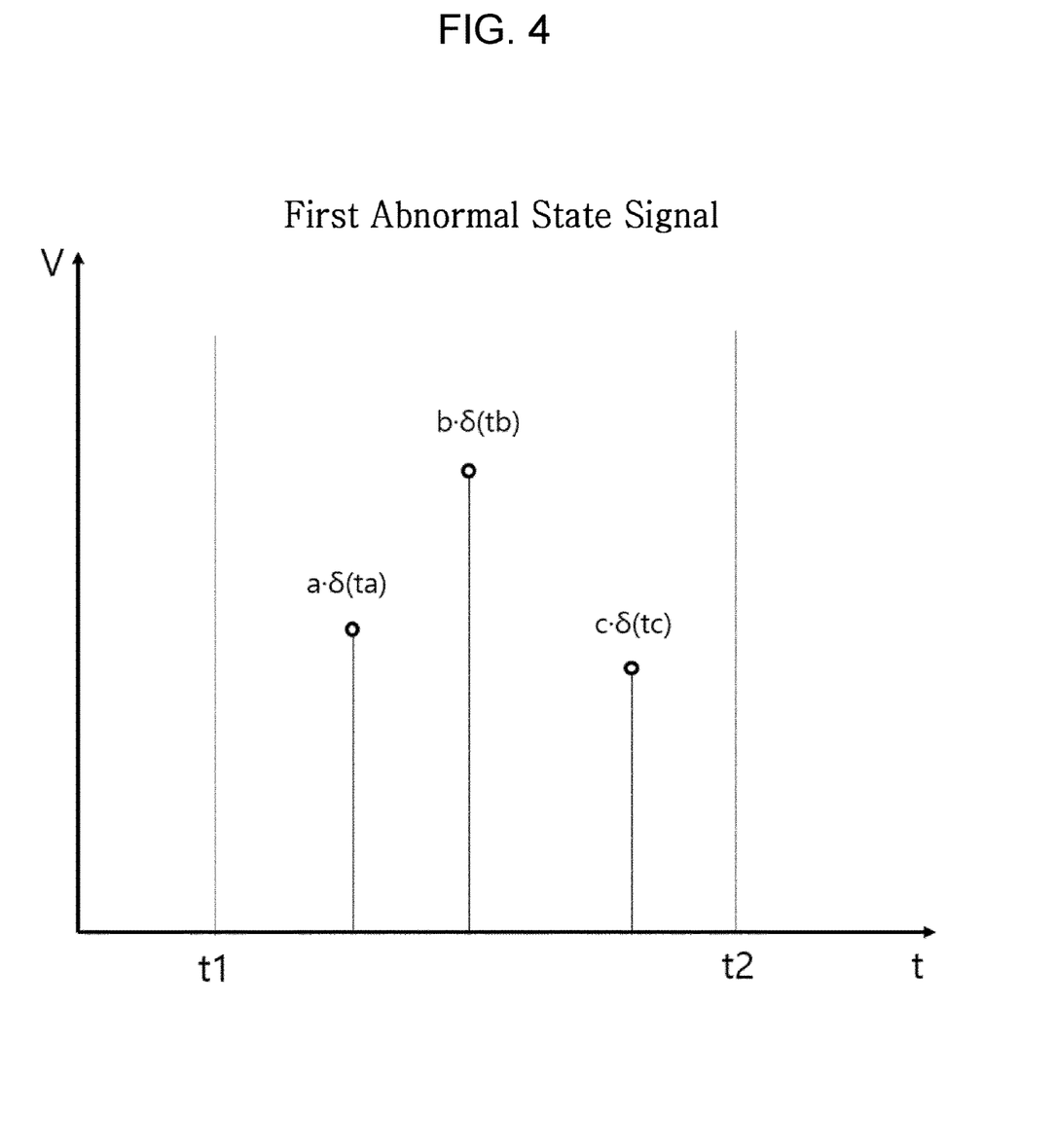
FIG. 4 is a view illustrating a first abnormal state signal and a second abnormal state signal according to an embodiment of the present disclosure.

Next, the abnormal state variable value recognizing operation in which the processor 10 recognizes a first variable value and a second variable value is described with reference to FIG. 4. Here, in the method of recognizing the first variable value and the second variable value, the processor 10 may receive the first variable value and the second variable value through the input unit 100 or the processor 10 may generate the first variable value and the second variable value from the normal state data set.

The first variable value and the second variable value may be input by the user through the input unit 100. As is described below, the first variable value and the second variable value may refer to a coefficient value or a variable value for a constant function. Therefore, the user may input a coefficient value or variable value that may be applied to the corresponding function through the input unit 100 and transfer the coefficient value or variable value to the processor 10.

The first variable value and the second variable value may be newly generated by the processor 10 based on the normal state data set. As described above, although the input value of the normal state data set is changed within a predetermined range, the first variable value or the second variable value may be generated by changing the value of the normal state data set according to a predetermined rule or by a command stored in the processor 10.

The processor 10 may further recognize a third variable value. Here, the third variable value may be input by the user through the input unit 100. Like the first variable value or the second variable value, the third variable value may refer to a coefficient value or a variable value for a constant function.

Next, the abnormal state signal generating operation in which the processor 10 generates a first abnormal state signal corresponding to the first normal state signal by applying the first variable value to an impulse function and generates a second abnormal state signal corresponding to the second normal state signal by applying the second variable value to a Gaussian distribution function is described.

The first variable value may refer to a coefficient value or a variable value for the impulse function. Accordingly, the processor 10 may generate the first abnormal state signal by multiplying the first variable value by the impulse function or by applying a variable value. As shown in FIG. 4, three impulse functions, that is, abnormal state signals, exist between time point t1 and time point t2. The first abnormal state signal refers to a signal having a coefficient value a and an impulse signal at time ta. The second abnormal state signal refers to a signal having a coefficient value b and an impulse signal at time tb. Similarly, the third abnormal state signal refers to a signal having a coefficient value c and an impulse signal at time tc.

Figure 5:
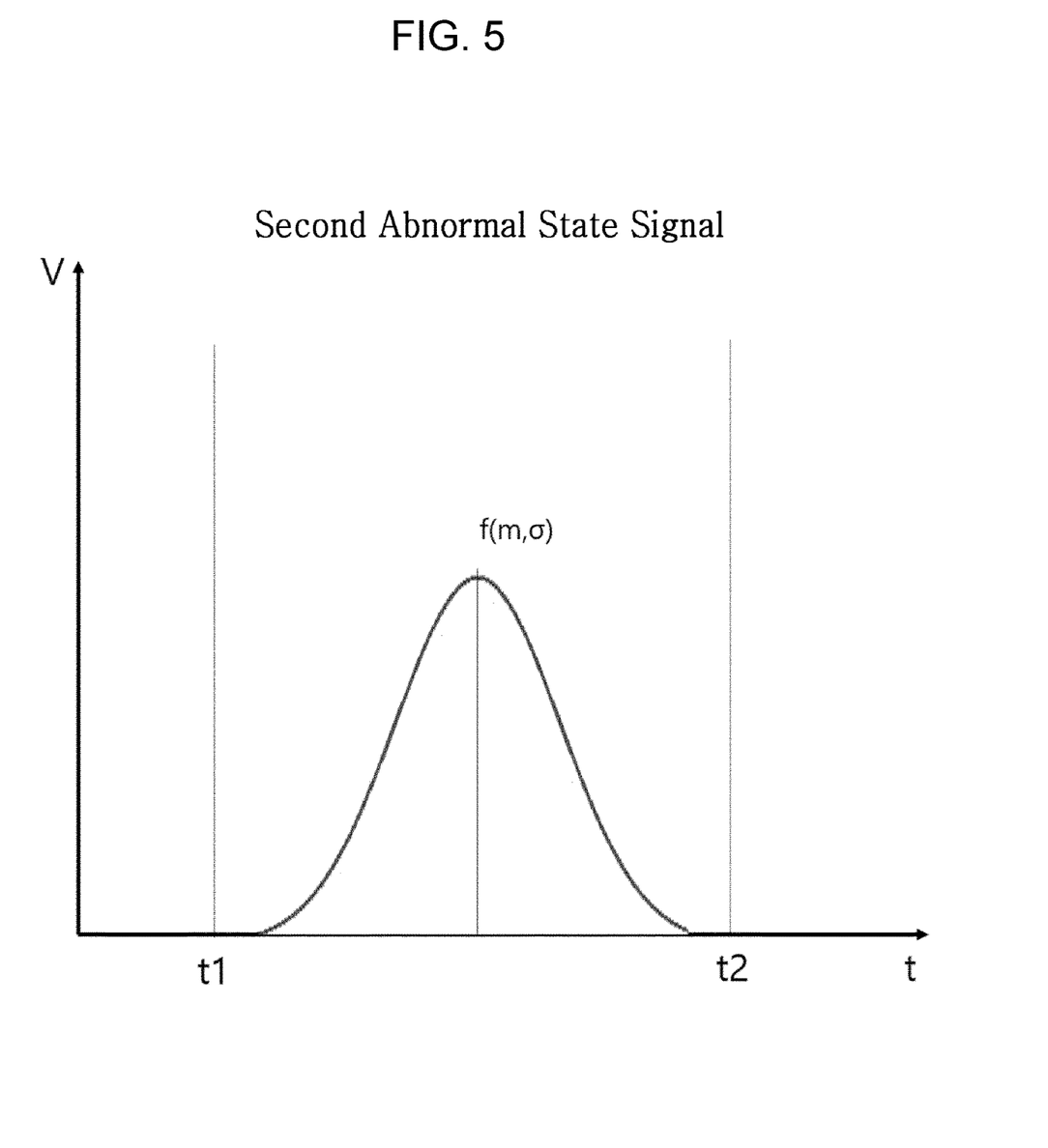
FIG. 5 is a view illustrating a second abnormal state signal according to an embodiment of the present disclosure.

The second variable value may refer to a mean or variance of the Gaussian distribution function. Accordingly, the processor 10 may generate the second abnormal state signal by applying the second variable value to the Gaussian distribution function. As shown in FIG. 5, an abnormal state signal following the Gaussian distribution exists between time point t1 and time point t2. This signal refers to a signal in the form of a Gaussian distribution with mean m and variance a.

Here, the first variable value and the second variable value may include information on a time at which the first abnormal state signal and the second abnormal state signal are generated and frequency of the first abnormal state signal and the second abnormal state signal, respectively.

As described above, the processor 10 may recognize the third variable value and apply a step function. In this case, whether the processor 10 applies the third variable value and the step function may be determined based on at least one of the first normal state signal and the second normal state signal.

Next, an abnormal state data set generating operation in which the processor generates an abnormal state data set based on the first abnormal state signal and the second abnormal state signal is described. The processor 10 generates an abnormal state data set obtained by converting the generated first abnormal state signal and the generated second abnormal state signal into constant data. Unlike normal state data sets, the abnormal state data set may be considered to reflect a measured value that may be generated in a situation in which a detection element (e.g., carbon dioxide) detected by the sensor is abnormal, independent of an environment in which the sensor is installed. In addition, the abnormal state signal may be regarded as a signal out of a range of the normal state.

The processor 10 may apply the third variable value, instead of at least one of the first variable value and the second variable value, to at least one of the first abnormal state signal and the second abnormal state signal and apply the step function, instead of at least one of the impulse function and the Gaussian distribution function. Accordingly, the function to which the first variable value, the second variable value, and the third variable value are applied may include the stem function in addition to the impulse function and the Gaussian distribution function. In the present disclosure, only the three functions described above are described, but any function may be used as long as the function generates an abnormal state signal as considered to be obvious by a person skilled in the art.

Figure 6:
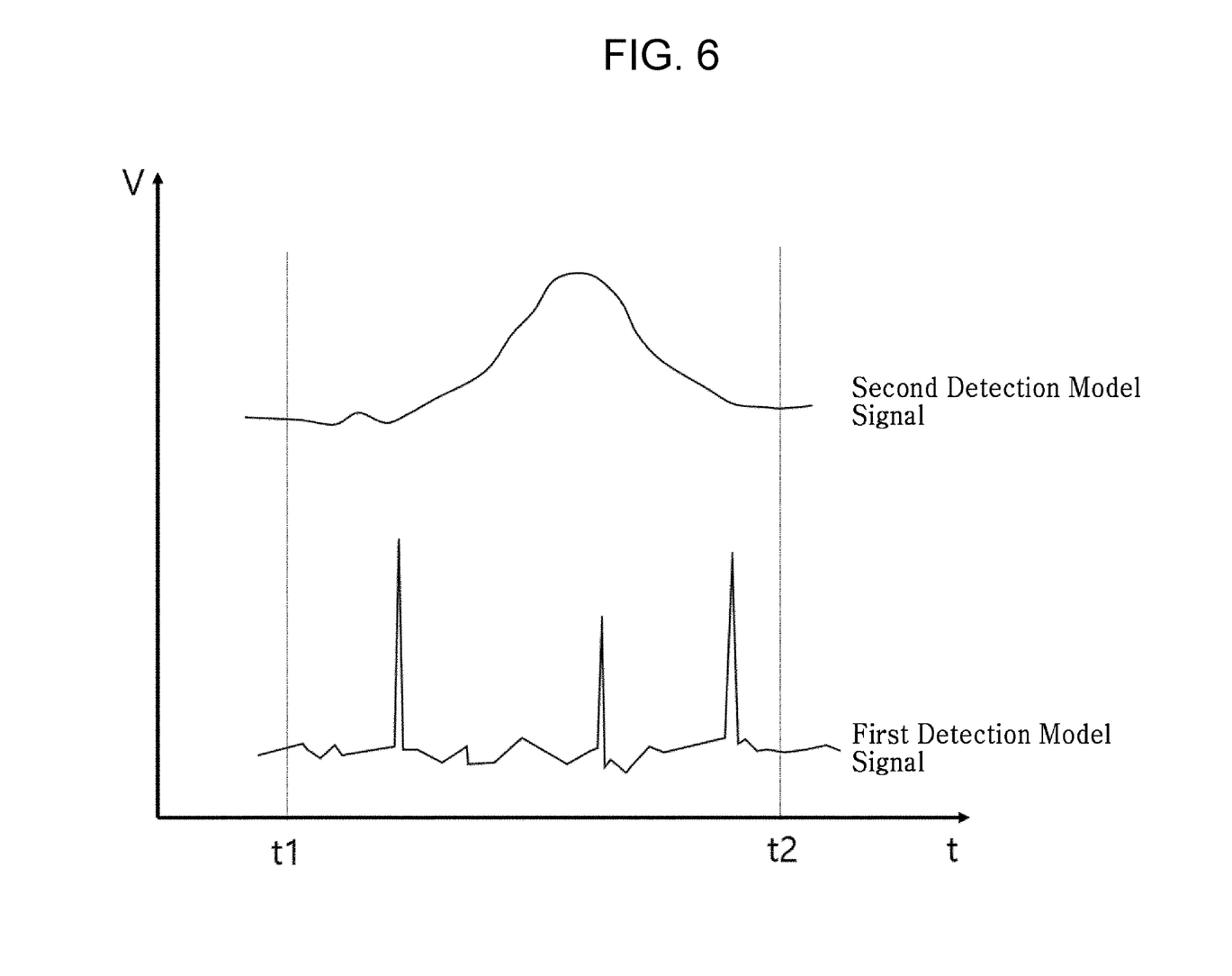
FIG. 6 is a view illustrating a combination of a second normal state signal and a second abnormal state signal according to an embodiment of the present disclosure.

Next, a learning set generating operation in which the processor 10 generates a detection model learning set for generating an abnormal state detection model by combining the normal state data set and the abnormal state data set is described with reference to FIG. 6. As shown in FIG. 6, the first detection model signal is a combination of the first normal state signal of the normal state data set and the first abnormal state signal of the abnormal state data set according to a predetermined rule. Similarly, the second detection model signal is a combination of the second normal state signal of the normal state data set and the second abnormal state signal of the abnormal state data set according to a predetermined rule. Here, the method of combining the normal state signal and the abnormal state signal may be adding the signal values of the normal state signal and the abnormal state signal based on the same time point.

Next, an abnormal state detection model generating operation in which the processor 10 generates an abnormal state detection model based on a detection model learning set is described. The processor 10 may generate an abnormal state detection model based on k-mean clustering by utilizing the generated detection model learning set. That is, since the detection model learning set includes the normal state signal and the abnormal state signal, the processor 10 may determine the normal state and the abnormal state with respect to various input values input by the sensor afterwards. Here, k-mean clustering refers to an algorithm grouping given signals into k clusters.

Next, a test set generating operation in which the processor 10 generates a detection model test set by combining the normal state data set and the abnormal state data set is described. From the user's point of view, it may be necessary to test whether the processor 10 to which the abnormal state detection model is applied operates normally. Therefore, a detection model test set capable of testing the abnormal state detection model may be generated by combining the normal state data set and the abnormal state data set. Here, the detection model learning set and the detection model test set have different combinations of the normal state data set and the abnormal state data set. That is, the normal state signals and the abnormal state signals included in the detection model learning set and the detection model test set may have different ratios or distributions.

Next, an abnormal state detection model testing step in which the processor 10 tests the abnormal state detection model using the detection model test set is described. As described above, the detection model test set may test the abnormal state detection model. Through this, the user may know whether the abnormal state detection model operates normally.

The computer system 1 according to the present disclosure may be a fire detection system. The sensors described above may detect temperature, humidity, infrared rays, a concentration of carbon dioxide, etc. to detect a fire, so that the processor 10 may determine a fire risk. The fire risk determined by the processor 10 may be transferred to the user.

The technical features disclosed in each embodiment of the present disclosure are not limited only to the corresponding embodiment, and the technical features disclosed in each embodiment may be combined and applied to different embodiments unless they are mutually incompatible.

In the above, embodiments of the method of generating an abnormal state detection model according to the present disclosure have been described. The present embodiment is not limited to the embodiments and the accompanying drawings described above, and various modifications and variations may be made from the point of view of those skilled in the art to which the present embodiment pertains. Accordingly, the scope of the present embodiment should be defined not only by the claims of the present disclosure, but also by the claims and their equivalents.

What is claimed is:

1. A method of generating an abnormal state detection model by a computer system including a processor for receiving signals from a first sensor and a second sensor, the method comprising:
  a normal state receiving operation in which the processor receives a first normal state signal detected by the first sensor for a predetermined time and a second normal state signal detected by the second sensor for the predetermined time;
  a normal state data set generating operation in which the processor generates a normal state data set based on the first normal state signal and the second normal state signal;
  an abnormal state variable value recognizing operation in which the processor recognizes a first variable value and a second variable value;
  an abnormal state signal generating operation in which the processor generates a first abnormal state signal and a second abnormal state signal, wherein the first abnormal state signal is generated by applying the first variable value to an impulse function, and the second abnormal state signal is generated by applying the second variable value to a Gaussian distribution function;
  an abnormal state data set generating operation in which the processor generates an abnormal state data set based on the first abnormal state signal and the second abnormal state signal;
  a learning set generating operation in which the processor generates a detection model learning set for generating an abnormal state detection model by combining the normal state data set and the abnormal state data set, wherein the detection model learning set includes a first detection model signal, which is generated based on the first normal state signal and the first abnormal state signal, and a second detection model signal, which is generated based on the second normal state signal and the second abnormal state signal; and
  an abnormal state detection model generating operation in which the processor generates an abnormal state detection model based on the detection model learning set.

2. The method of claim 1, wherein
the first sensor is an infrared sensor and the second sensor is a carbon dioxide detection sensor.

3. The method of claim 2, wherein
the first abnormal state signal is a signal that models a signal detecting an occurrence of at least one of flame, spark, and arc by the first sensor.

4. The method of claim 2, wherein
the second abnormal state signal is a signal that models a signal detecting an occurrence of at least one of smoke and combustion gas by the second sensor.

5. The method of claim 2, wherein
the computer system is a fire detection system.

6. The method of claim 1, wherein
the first variable value is a coefficient value of the impulse function, and
in the abnormal state signal generating operation, the processor generates the first abnormal state signal by multiplying the first variable value by the impulse function.

7. The method of claim 1, wherein
the second variable value is at least one of a mean and a variance of the Gaussian distribution function, and
in the abnormal state signal generating operation, the processor specifies a form of the Gaussian distribution function by applying the second variable value.

8. The method of claim 1, wherein
the first variable value and the second variable value each include information on an occurrence time and frequency of the first abnormal state signal and the second abnormal state signal.

9. The method of claim 1, further comprising:
a test set generating operation in which the processor generates a detection model test set by combining the normal state data set and the abnormal state data set; and
an abnormal state detection model test operation in which the processor tests the abnormal state detection model using the detection model test set.

10. The method of claim 9, wherein
the detection model learning set and the detection model test set have different combination ratios of the normal state data set and the abnormal state data set.

11. The method of claim 1, wherein
the abnormal state variable value recognizing operation includes an operation in which the processor receives the first variable value and the second variable value input to an input unit.

12. The method of claim 1, wherein
the abnormal state variable value recognizing operation includes an operation in which the processor generates the first variable value and the second variable value from the normal state data set.

13. The method of claim 1, wherein,
in the variable value recognizing operation, the processor further recognizes a third variable value, and in the abnormal state signal generating operation, the processor applies the third variable value instead of at least one of the first variable value and the second variable value in at least one of the first abnormal state signal and the second abnormal state signal, and applies a step function instead of at least one of the impulse function and the Gaussian distribution function.

14. The method of claim 13, wherein
whether the processor applies the third variable value and the step function is determined based on at least one of the first normal state signal and the second normal state signal in the abnormal state signal generating operation.

15. A computer system for generating an abnormal state detection model, the computer system comprising:
an input unit;
a communication unit; and
a processor configured to receive a signal from a first sensor and a second sensor,
wherein the processor is configured to
receive a first normal state signal detected by the first sensor for a predetermined time and a second normal state signal detected by the second sensor for a predetermined time,
generate a normal state data set based on the first normal state signal and the second normal state signal,
receive a first variable value and a second variable value received by the input unit,
generate a first abnormal state signal, wherein the first abnormal state signal is generated by applying the first variable value to an impulse function,
generate a second abnormal state signal by applying the second variable value to a Gaussian distribution function,
generate an abnormal state data set based on the first abnormal state signal and the second abnormal state signal,
generate a detection model learning set for generating an abnormal state detection model by combining the normal state data set and the abnormal state data set, wherein the detection model learning set includes a first detection model signal, which is generated based on the first normal state signal and the first abnormal state signal, and a second detection model signal, which is generated based on the second normal state signal and the second abnormal state signal, and
generate an abnormal state detection model based on the detection model learning set.

* * * * *